(12) United States Patent
Muller

(10) Patent No.: US 8,583,234 B1
(45) Date of Patent: Nov. 12, 2013

(54) SYSTEM AND METHOD FOR LEFT ATRIAL PACING IN PATIENTS WITH DIASTOLIC HEART FAILURE

(75) Inventor: David Muller, Sicklerville, NJ (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/571,235

(22) Filed: Aug. 9, 2012

(51) Int. Cl.
*A61N 1/00* (2006.01)

(52) U.S. Cl.
USPC .......................................................... 607/25

(58) Field of Classification Search
USPC .................................................... 607/25, 3, 9
See application file for complete search history.

(56) References Cited

U.S. PATENT DOCUMENTS

| | | | | |
|---|---|---|---|---|
| 6,519,493 | B1 | 2/2003 | Florio et al. | 607/9 |
| 6,915,162 | B2 | 7/2005 | Noren et al. | 607/23 |
| 7,076,300 | B1 | 7/2006 | Kroll et al. | 607/14 |
| 7,113,822 | B1 | 9/2006 | Kroll | 607/14 |
| 7,289,847 | B1 | 10/2007 | Gill et al. | 607/5 |
| 7,363,077 | B1 | 4/2008 | Min et al. | 607/9 |
| 7,416,529 | B2 | 8/2008 | Hedberg | 600/485 |
| 7,509,169 | B2 | 3/2009 | Eigler et al. | 607/27 |
| 7,526,338 | B1 | 4/2009 | Gill et al. | 607/18 |
| 7,643,878 | B1 | 1/2010 | Muller et al. | 607/9 |
| 7,761,160 | B2 | 7/2010 | Muller et al. | 607/25 |
| 7,792,581 | B2 | 9/2010 | Hettick et al. | |
| 7,794,404 | B1 | 9/2010 | Gutfinger et al. | 600/486 |
| 7,850,616 | B1 | 12/2010 | Gill et al. | 600/526 |
| 7,869,871 | B2 | 1/2011 | Salo et al. | 607/9 |
| 8,135,468 | B2 | 3/2012 | Gutfinger et al. | 607/28 |
| 2006/0149155 | A1 | 7/2006 | Hedberg | 600/508 |
| 2006/0173502 | A1* | 8/2006 | Baynham | 607/9 |
| 2007/0203522 | A1 | 8/2007 | Hettrick et al. | |
| 2007/0239219 | A1 | 10/2007 | Salo et al. | |
| 2007/0276443 | A1* | 11/2007 | Shafer et al. | 607/3 |
| 2008/0262365 | A1 | 10/2008 | Bjorling | 600/515 |
| 2009/0018597 | A1 | 1/2009 | Wenzel | 607/23 |
| 2010/0069990 | A1 | 3/2010 | Muller et al. | |
| 2010/0256701 | A1 | 10/2010 | Muller | 607/14 |
| 2011/0208077 | A1 | 8/2011 | Soriano et al. | 600/513 |

FOREIGN PATENT DOCUMENTS

| WO | WO 2007/101229 | 9/2007 |
|---|---|---|
| WO | WO 2007/115188 | 10/2007 |

OTHER PUBLICATIONS

Bordacher et al. "Echocardiographic Parameters of Ventricular Dyssynchrony Validation in Patients With Heart Failure Using Sequential Biventricular Pacing" JACC 2004 44 11 2175-2165.

Borlaug et al., "Diastolic relaxation and compliance reserve during dynamic exercise in heart failure with preserved ejection fraction", Heart 2011;97:964e969. doi:10.1136/hrt.2010.212787.

(Continued)

*Primary Examiner* — Robert N Wieland

(57) ABSTRACT

Techniques are provided for use with an implantable medical device for delivering left atrial (LA) pacing to address Diastolic Heart Failure, also referred to as Heart Failure with Preserved Ejection Fraction. In one example, pulse delivery times are selected for delivery of LA pacing pulses sufficient so that activation of the LA occurs when LA pressure (LAP) is lower than would occur in the absence of LA pacing. The pulse delivery times and also set so that subsequent activation of the right ventricle (RV) occurs when LAP is lower than would occur in the absence of LA pacing. LA pacing then is delivered by the implanted device at the selected pulse delivery times to mitigate Diastolic Heart Failure or to address other conditions.

8 Claims, 7 Drawing Sheets

(56) References Cited

OTHER PUBLICATIONS

Borlaug et al., "Impaired Chronotropic and Vasodilator Reserves Limit Exercise Capacity in Patients With Heart Failure and a Preserved Ejection Fraction", Circulation. 2006;114:2138-2147.

Burri et al. "Biatrial pacing improves atrial haemodynamics and atrioventricular timing compared with pacing from the right atrial appendage", Europace, doi:10.1093/europace/eur099.

Chung et al. "Cardiac resynchronization therapy may benefit patients with left ventricular ejection fraction >35%: a Prospect trial substudy", EJHF 2010;12:581-587.

Gottdiener et al. "Left Atrial Volume, Geometry, and Function in Systolic and Diastolic Heart Failure of Persons >65 Years of Age (The Cardiovascular Health Study)" Am J Cardiol 2006; 97:83-89.

Maass et al. "Importance of Heart Rate During Exercise for Response to Cardiac Resynchronization Therapy" JCE 2009; 20:773-780.

Penicka et al. "Cardiac resynchronization therapy for the causal treatment of heart failure with preserved ejection fraction: insight from a pressure—volume loop analysis" EJHF 2010;12:634-636.

Phan et al., "The pathophysiology of diastolic heart failure", f1000 Biology Reports 2010, 2:16.

Yu et al. "Left Ventricular Reverse Remodeling but Not Clinical Improvement Predicts Long-Term Survival After Cardiac Resynchronization Therapy" Circ 2005; 112:1580-1586.

\* cited by examiner

SYSTEM AND METHOD FOR LEFT ATRIAL PACING IN PATIENTS WITH DIASTOLIC HEART FAILURE

TECHNICAL FIELD

The invention generally relates to implantable medical devices such as pacemakers, implantable cardioverter-defibrillators (ICDs) or cardiac resynchronization therapy (CRT) devices and in particular to techniques for pacing the heart to address diastolic heart failure (DHF).

BACKGROUND

DHF—also referred to as heart failure with preserved ejection fraction (HF-PEF)—is a condition wherein systolic heart function is generally preserved but diastolic function is compromised, i.e. there is a significant degree of diastolic dysfunction. Diastolic dysfunction generally refers to an abnormality in the ability of the heart to fill during diastole, which is the phase of the cardiac cycle when the ventricles relax and fill with blood prior to contraction. At present, implantable medical devices are not adequately equipped to treat DHF. However, clinical evidence is emerging that CRT may show benefit in the DHF patient population. Some early CRT studies have shown the benefit of CRT therapy for patients inadvertently included in CRT trials with significant improvements in functional class and symptoms. [See, Cleland et al., "Long-term effect of cardiac resynchronisation in patients reporting mild symptoms of heart failure: a report from the CARE-HF study", Heart 2008; 94:278-283] An additional recent publication from the PROSPECT trial found that 24% of patients had an ejection fraction (EF) below 35% and, even though this group had lower left ventricular (LV) volumes and shorter surface electrocardiogram (ECG) QRS duration, outcomes were not significantly different from the low EF group. [See, Chung et al. "Cardiac resynchronization therapy may benefit patients with left ventricular ejection fraction >35%: a PROSPECT trial substudy", EJHF 2010; 12:581-587 and Penicka et al. "Cardiac resynchronization therapy for the causal treatment of heart failure with preserved ejection fraction: insight from a pressure-volume loop analysis" EJHF 2010; 12:634-636] This included reduced left ventricular (LV) end diastolic volumes, which are associated with a mortality and morbidity benefit. [See, Yu et al. "Left Ventricular Reverse Remodeling but Not Clinical Improvement Predicts Long-Term Survival After Cardiac Resynchronization Therapy" Circ 2005; 112:1580-1586.]

Programming of the atrioventricular (AV) interval in CRT patients has been shown to benefit outcomes of patients. The effects of intra-atrial delay based on the position of a right atrial (RA) lead has been shown to be potentially deleterious to patient outcomes causing intra-atrial dyssynchrony similar to that seen in the ventricles. [See, Maass et al. "Importance of Heart Rate During Exercise for Response to Cardiac Resynchronization Therapy" JCE 2009; 20:773-780.] Left atrial size (thus intra atrial delay) has also been shown to have an impact on the progression of congestive heart failure (CHF) specifically DHF. [See, Gottdiener et al. "Left Atrial Volume, Geometry, and Function in Systolic and Diastolic Heart Failure of Persons >65 Years of Age (The Cardiovascular Health Study)" Am J Cardiol 2006; 97:83-89.] Careful optimization of AV timing has been shown in numerous studies to benefit diastolic parameters. [See, for example, Chan et al. "Tissue Doppler Guided Optimization of A-V and V-V Delay of Biventricular Pacemaker Improves Response to Cardiac Resynchronization Therapy in Heart Failure Patients" J of Cardiac Failure 2004; 10, 4 (suppl.): S72 (abstract 199); Bordacher et al. "Echocardiographic Parameters of Ventricular Dyssynchrony Validation in Patients With Heart Failure Using Sequential Biventricular Pacing" JACC 2004 44 11 2175-2165; O'Donnell et al. "Long-term variations in optimal programming of cardiac resynchronization therapy devices" PACE 2005; 28:S24-S26; and Zhang et al. "The role of repeating optimization of atrioventricular interval during interim and long-term follow-up after cardiac resynchronization therapy" Volume 124, Issue 2, 29 Feb. 2008, Pages 211-217). In addition, a large group of DHF patients suffer from chronotropic incompetence, which can be readily addressed via otherwise conventional atrial pacing (i.e. atrial pacing wherein stimulation pulses are delivered to the right atrium (RA) via an RA lead.) Note that the presence of chronotropic incompetence has also been shown an important predictor to CRT response. [See, Borlaug et al. "Echocardiographic Parameters of Ventricular Dyssynchrony Validation in Patients With Heart Failure Using Sequential Biventricular Pacing Impaired Chronotropic and Vasodilator Reserves Limit Exercise Capacity in Patients With Heart Failure and a Preserved Ejection Fraction" Circ. 2006; 114:2138-2147]

Nevertheless, there is still a significant need to provide effective pacing techniques for use by implantable medical devices within DHF patients and it is to this end that aspects of the invention are generally directed.

SUMMARY

In accordance with exemplary embodiments, techniques are provided for use with an implantable medical device having a stimulation electrode positioned near the left atrium (LA) of a patient for delivering pacing stimulation to the LA. In one example, electrical cardiac signals are sensed and then pulse delivery times are determined for delivery of LA pacing pulses sufficient so that activation of the LA occurs when LA pressure (LAP) is lower than would occur in the absence of LA pacing and also so that subsequent activation of the right ventricle (RV) occurs when LAP is likewise lower than would occur in the absence of LA pacing. LA pacing is then delivered using the stimulation electrode positioned near the LA at the determined pulse delivery times to mitigate DHF or to address other conditions.

In an illustrative example, the LA pulses are delivered using the proximal electrode of an LV lead implanted via the coronary sinus (CS) where the proximal electrode is positioned sufficiently close to the LA to trigger depolarization of the LA. The LA pulses are delivered prior to intrinsic depolarization of the atria. In this regard, during the slow filling phase of diastole of the preceding heart beat, LAP slowly builds due to blood flowing into the LA along the pulmonary vein from the lungs. The LA pulses are advantageously timed for delivery relatively early during this interval so that LAP will be comparatively low at the time of the resulting paced atrial contractions. That is, LAP will be lower at the time of the paced atrial contraction than it would be at the time of an intrinsic atrial contraction if no LA pacing were delivered. Since the LA thereby contracts at a time when LAP is comparatively low, this allows for faster and earlier filling of the LV, which is believed to be beneficial within DHF patients who often suffer elevated LAP due to decreased LV compliance or other factors.

The LA pulse thus triggers contraction of the LA, which is followed shortly thereafter by contraction of the RA via left-to-right conduction. The electrical activation of the atria then propagates to the ventricles resulting in activation of both the left and right ventricles. In particular, the RV contracts to pump blood through the pulmonary artery into the lungs and ultimately via the pulmonary vein into the LA, which has a lower pressure than would otherwise occur in the absence of the LA pacing. That is, by pacing the LA early in the cardiac cycle (when LAP is comparatively low), the LA will begin to eject blood into the LV relatively early and so LAP will then begin to drop relatively early, thereby allowing the RV to pump blood into the pulmonary system with less resistance (since, ultimately, the resistance the RV experiences is affected by the pressure in the LA at the time the RV contracts).

Still further, there is a built in time delay as a paced conduction wavefront travels from left to right within the heart. This allows for more emptying in the left side of the heart, so by the time the RV begins it mechanical contraction, the LV has already begun its contraction and thus the LV pressure drop begins and completes earlier. Since the left and right pressures are tied together, the RV will thereby have less pressure to overcome as the left starts and finishes earlier. In this manner, with properly timed LA pacing (as opposed to RA pacing, biatrial pacing or no pacing), by the time the RV ejects into the pulmonary circuit, the forward flow requires less pressure to the advance blood through the pulmonary circuit than would otherwise occur. The net effect is reduced pulmonary pressure and hence reduced congestion in heart failure patients, decreased LAP since the LA is unloaded via earlier activation due to the LA pacing, thus providing better forward-loading of the LV, at least within some patients. This can also benefit LV end diastolic volume (LV EDV).

System and method examples are described herein below.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
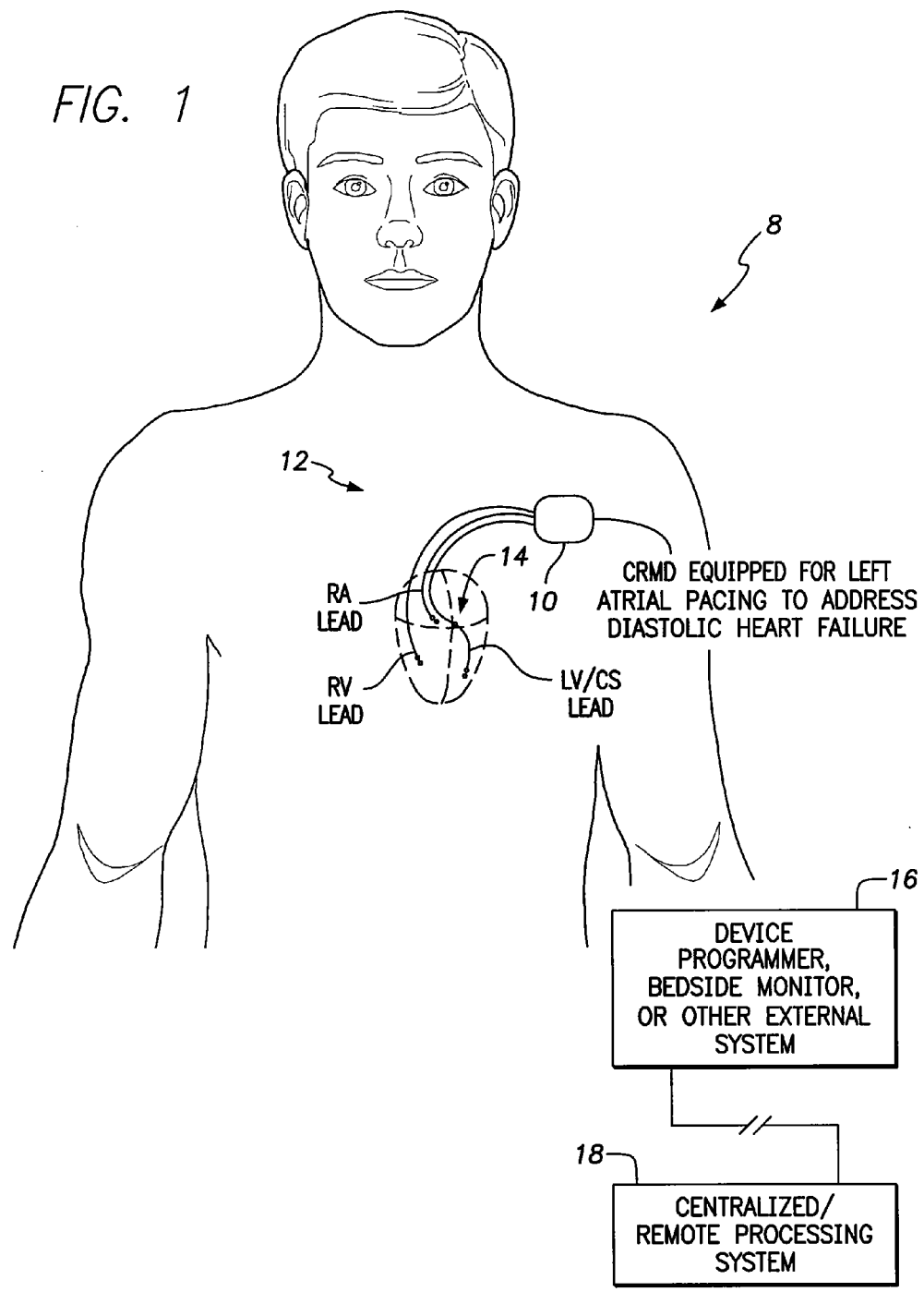
FIG. 1 illustrates pertinent components of an implantable medical system having a cardiac rhythm management device (CRMD) equipped to deliver LA pacing to address DHF or other conditions.

FIG. 1 illustrates an implantable medical system 8 capable of delivering LA pacing to address DHF or other conditions. To this end, system 8 includes a CRMD capable of delivering atrial pacing pulses to the LA via the electrodes of one or more cardiac sensing/pacing leads 12 implanted on or within the heart of the patient. In FIG. 1, three exemplary leads are shown in stylized form: an RV lead; an RA lead and an LV/CS lead having a proximal electrode 14 positioned for stimulating the LA. A more complete illustration of an exemplary set of leads is provided in FIG. 7. As will be described in detail below, atrial pacing pulses are delivered using electrode 14 relatively early in the cardiac cycle to achieve certain benefits pertaining to reduced LAP, particularly for use within DHF patients (i.e. patients with HF-PEF) but the LA pacing might be advantageously exploited within other patients as well or to achieve other ends. Additionally, the CRMD may perform a wide variety of other pacing or defibrillation functions such as delivering pacing is response to arrhythmias or generating and delivering shocks in response to atrial or ventricular fibrillation.

Warning signals pertaining to DHF or other issues may be generated using an internal warning device within the CRMD or an external system 16, which can be a device programmer, bedside monitor or other suitable system. The internal warning device (not shown in FIG. 1) may be a vibrating device or a "tickle" voltage device that, in either case, provides perceptible stimulation to the patient to alert the patient. The external system may provide audible or visual alarm signals to alert the patient, as well as any appropriate textual or graphic displays. Diagnostic information pertaining to LA pacing or other matters may be stored within the CRMD for transmission to the external system for review by a clinician. The clinician may adjust the operation of the CRMD to activate, deactivate or otherwise control any therapies that are automatically applied. In addition, the external system may be directly networked with a centralized computing system 18 for relaying warnings or diagnostic information, where appropriate. The centralized system may include such systems as the HouseCall™ system or the Merlin@home/Merlin.Net system of St. Jude Medical.

Hence, FIG. 1 provides an overview of an implantable system for delivering LA pacing and further capable of generating appropriate warnings, controlling therapy, etc. Embodiments may be implemented that do not necessarily perform all of these functions. Systems provided in accordance with the invention need not include all the components shown in FIG. 1 such as the external system or might be equipped with other components that are not shown. No attempt is made herein to describe all possible combinations of components that may be provided in accordance with the general principles of the invention. Also, note that, the particular shape, size and locations of the implanted components shown in FIG. 1 are merely illustrative and may not necessarily correspond to actual implant locations. In particular, preferred implant locations for the leads are more precisely illustrated in FIG. 7.

LA Pacing Techniques

Figure 2:
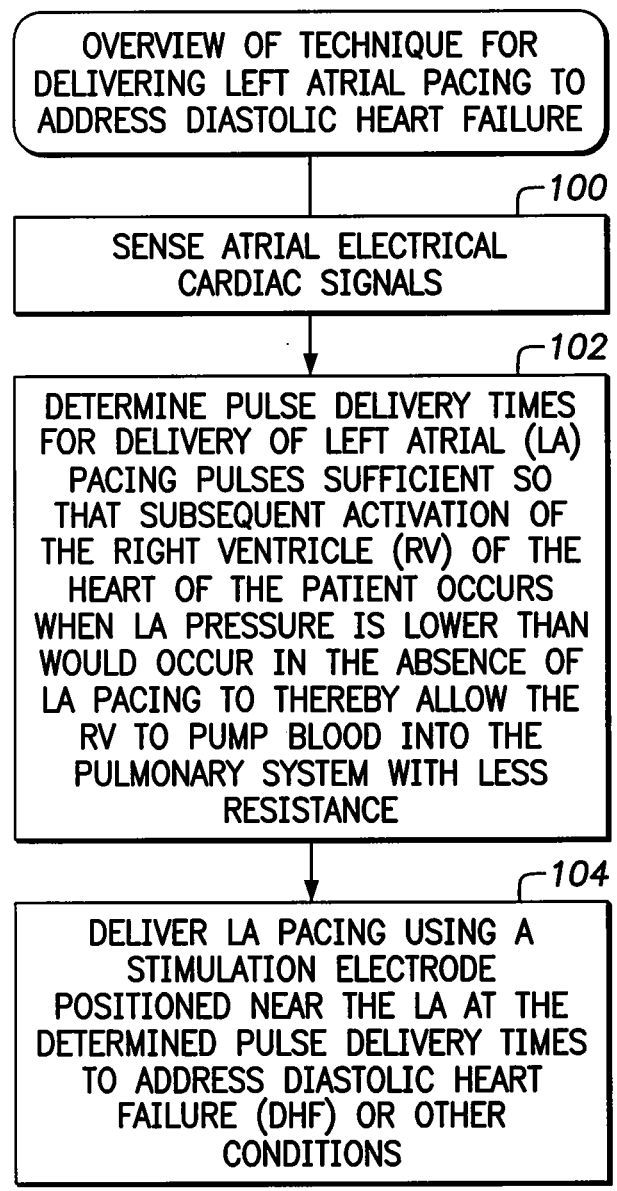
FIG. 2 provides an overview of the LA pacing technique performed by the system of FIG. 1.
Figure 3:
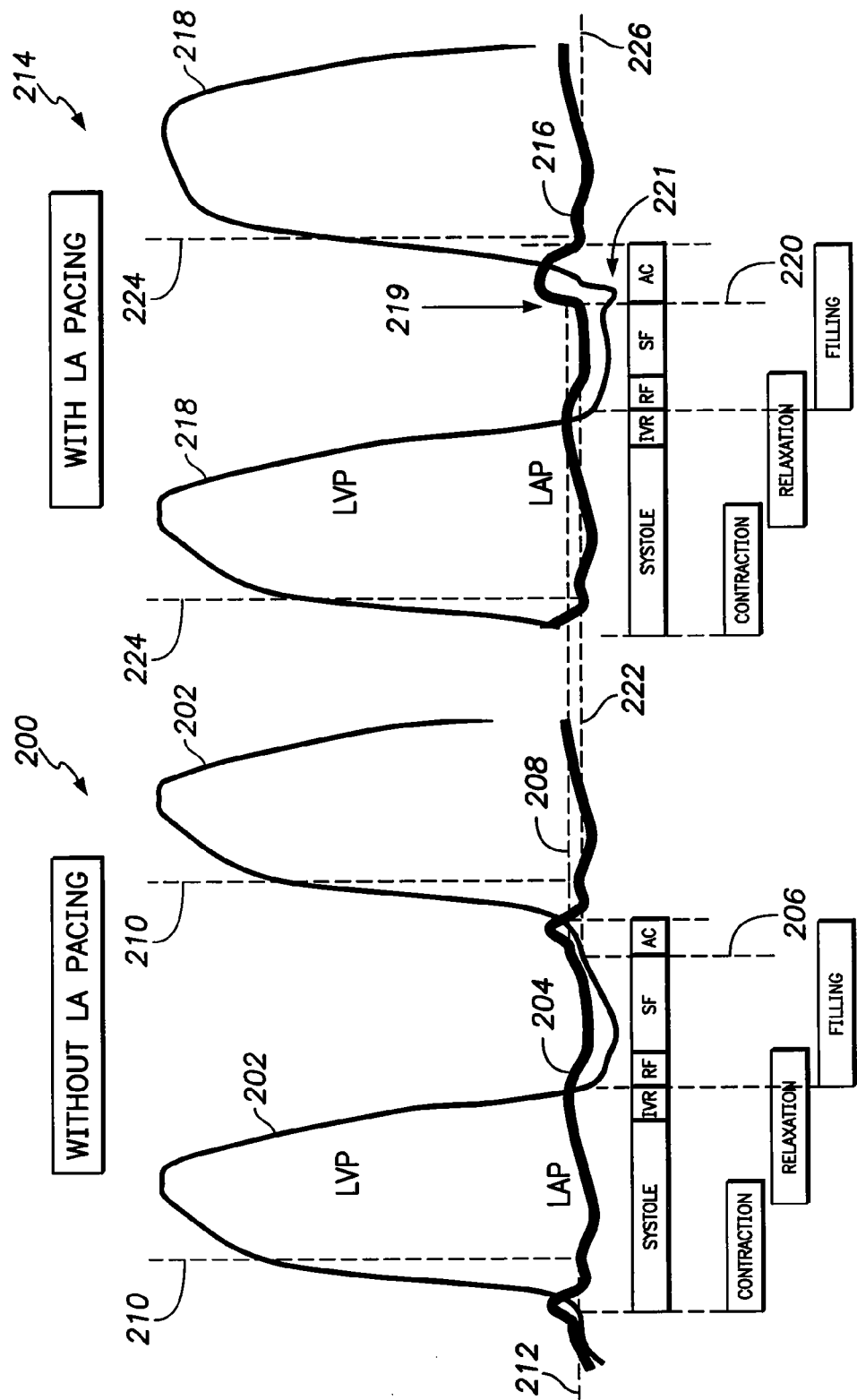
FIG. 3 is a stylized graph of exemplary pressure traces, illustrating advantageous features of the general technique of FIG. 2.
Figure 4:
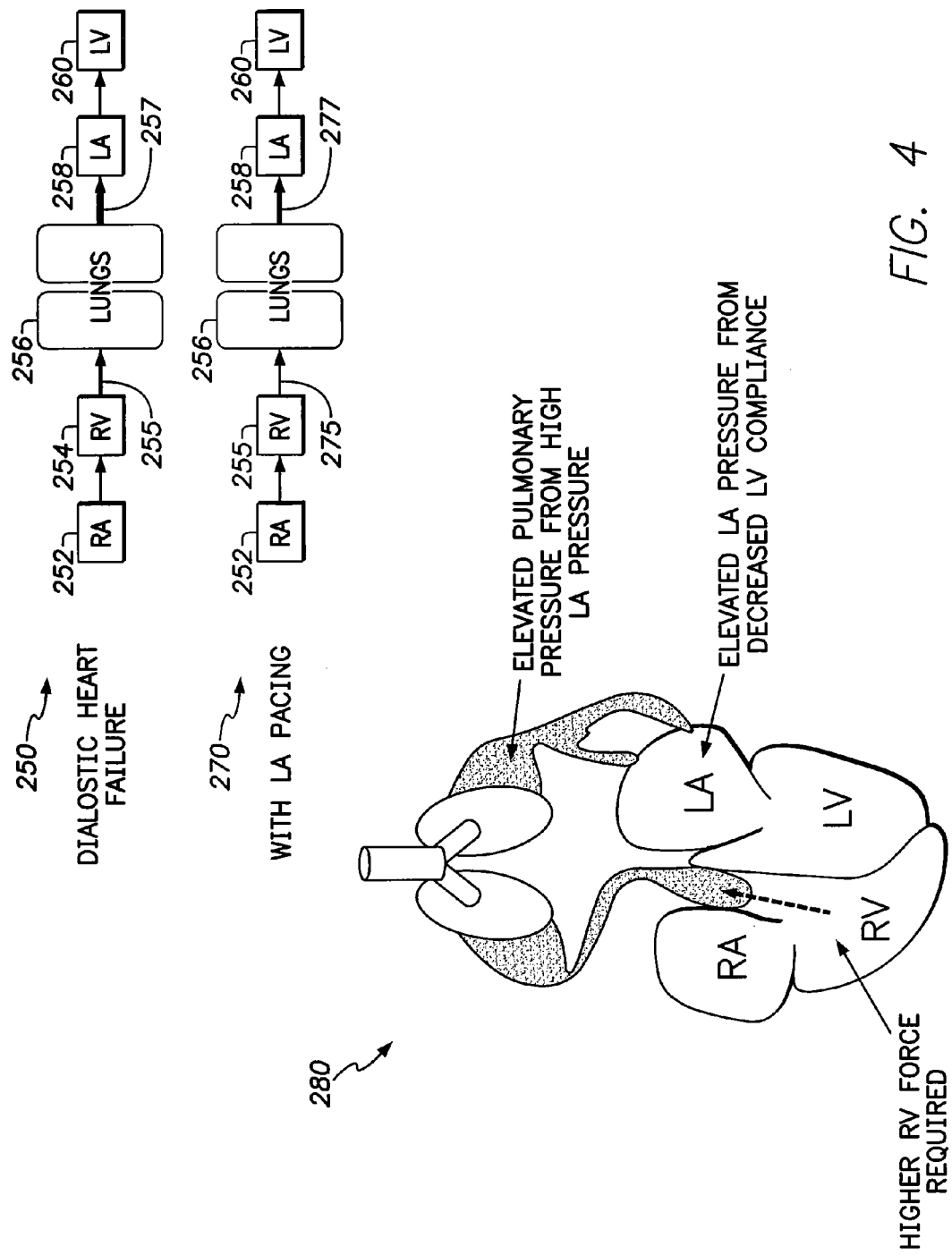
FIG. 4 provides schematic illustrations of blood flow through the cardiopulmonary system, further illustrating advantageous features of the general technique of FIG. 2.

FIGS. 2-4 generally illustrate techniques for controlling LA pacing that may be employed by the system of FIG. 1 or other suitably equipped systems. Beginning at step 100, the CRMD senses electrical cardiac signals including atrial signals and, at step 102, the device determines pulse delivery times for delivery of LA pacing pulses sufficient so that subsequent activation of the RV of the heart of the patient occurs when LAP is lower than would occur in the absence of LA pacing, thereby allowing the RV to pump blood into the pulmonary system with less resistance (within at least some patients). As already mentioned, early pacing of the LA also causes the LA to contract at a time when LAP is lower than it would be in the absence of LA pacing, thereby allowing for faster and earlier filling of the LV, which may also be beneficial within DHF patients who often suffer elevated LAP. At step 104, the device then delivers LA pacing using a stimulation electrode positioned near the LA (such as the proximal electrode of a LV/CD lead) at the determined pulse delivery times to mitigate DHF or other conditions.

As already summarized, the LA pacing pulses are timed to trigger contraction of the LA, followed shortly thereafter by contraction of the RA via left-to-right conduction. The electrical activation of the atria then propagates to the ventricles resulting in activation of both the left and right ventricles. The RV contracts to pump blood through the pulmonary artery into the lungs and ultimately via the pulmonary vein into the LA, which has a lower pressure than would otherwise occur in the absence of the LA pacing. Hence, by pacing the LA early in the cardiac cycle when LAP is comparatively low, the LA will begin to eject blood into the LV relatively early so that LAP will then begin to drop relatively early, thereby allowing the RV to pump blood into the pulmonary system with less resistance. Still further, given the built in time delay as the paced conduction wavefront travels from left to right within the heart, LA pacing allows for more emptying in the left, so by the time the RV begins it mechanical contraction, the LV has already begun its contraction and thus the LV pressure drop begins and completes earlier. Since the left and right pressures are tied together, the RV will thereby have less pressure to overcome as the left starts and finishes earlier (at least within some patients). Hence, with properly timed LA pacing, by the time the RV ejects into the pulmonary circuit, forward flow requires less pressure to the advance blood through the pulmonary circuit than would otherwise occur in the absence of the LA pacing. The net effect is reduced pulmonary pressure and decreased LAP, thus providing better forward-loading of the LV, at least within some patients. This can also benefit LV EDV.

FIG. 3 provides graphs of LAP and ventricular pressure (specifically LV pressure (LVP)) for cardiac cycles for an exemplary patient. Note that these are stylized graphs with arbitrary pressure and time scales. The graphs are provided to highlight certain advantageous features of the LA pacing techniques described herein but do not necessarily illustrate unique pressure characteristics of DHF. Actual pressure traces may differ within DHF patients. The first graph 200 of FIG. 3 shows LAP 202 and LVP 204 varying over two cardiac cycles without LA pacing, and provides labels illustrating the phases of the cardiac cycle: systole and the four phases of diastole (isovolumetric relaxation (IVR), rapid filling (RF), slow filling (SF) and atrial contraction (AC)). As shown, the cardiac cycle may also be divided into contraction, relaxation and diastolic filling. Note that each of the phases of the cardiac cycle is dependent on effects of the preceding phase.

Within graph 200, during the slow filling phase of diastole of a preceding cardiac cycle, LAP gradually rises until an intrinsic depolarization occurs at time 206 resulting in atrial contraction and a sharp increase in LAP as the atria contract. Note that LAP is relatively high at the time of atrial contraction, as indicated by LAP level 208. LAP is also relatively high at the time of ejection of blood from the RV into the pulmonary circuit, as indicated by time 210 and LAP level 212. For comparison, graph 214 shows LAP 216 and LVP 218 over two cardiac cycles with LA pacing. Again, during the slow filling phase of the preceding cardiac cycle, LAP gradually rises. In this case, however, an LAP pulse 219 is delivered at time 220 to trigger atrial contraction. Note that LAP is relatively lower at the time of the paced atrial contraction as indicated by LAP level 222 in comparison with level 208 for the case of no LA pacing and further note that LVP is lower following the LA pulse than without LA pacing as indicated by downward LVP notch 221. As already explained, blood is ejected from the RV slightly earlier with LA pacing than without, as indicated by vertical lines 224. LAP is relatively lower at the time of ejection of blood from the RV as indicated by LAP level 226 (with LA pacing) as compared to LAP level 212 (without LAP pacing.) Again, note that these pressure levels are not necessarily to scale but are provided merely to illustrate features of the LA pacing techniques described herein. Actual comparative pressure differences may be greater within DHF patients for whom the LA pacing techniques described herein may be particularly helpful.

FIG. 4 provides schematic illustrations of blood flow through the heart to further illustrate advantageous features of the LA pacing techniques described herein, particularly for patients with DHF. A first blood flow schematic 250 shows blood flow for DHF (without LA pacing) from RA 252 to RV 254 then through lungs 256 into LA 258 and then LV 260. Due to DHF, resistance to blood flow from the RV into the lung is relatively high, as indicated by gray arrow 255. Resistance to blood flow from the lungs into the LA is even higher, as indicated by black arrow 257. In comparison, a second blood flow schematic 250 shows blood flow for DHF with LA pacing. By virtue of the LA pacing techniques described herein, resistance to blood flow from the RV into the lung is comparatively lower (than without LA pacing), as indicated by unshaded arrow 275. Resistance to blood flow from the lungs into the LA is likewise comparatively lower (than without LA pacing), as indicated by gray arrow 277. FIG. 4 also provides a stylized representation of a cardiopulmonary system 280 with DHF, particularly identifying that higher force is required to pump blood from the RV into the pulmonary artery due elevated pulmonary pressures, which are due to elevated LAP arising from decreased LV compliance or other factors associated with DHF.

For further information regarding the effects of pacing on the cardiopulmonary system see, for example: Doi et al., "Acute Hemodynamic Benefits of Bi-Atrial Atrioventricular Sequential Pacing With the Optimal Atrioventricular Delay" J Am Coll Cardiol, 2005; 46:320-326, doi:10.1016/j.jacc.2005.04.032, and Burri et al. "Biatrial pacing improves atrial haemodynamics and atrioventricular timing compared with pacing from the right atrial appendage", Europace, doi: 10.1093/europace/eur099.

Figure 5:
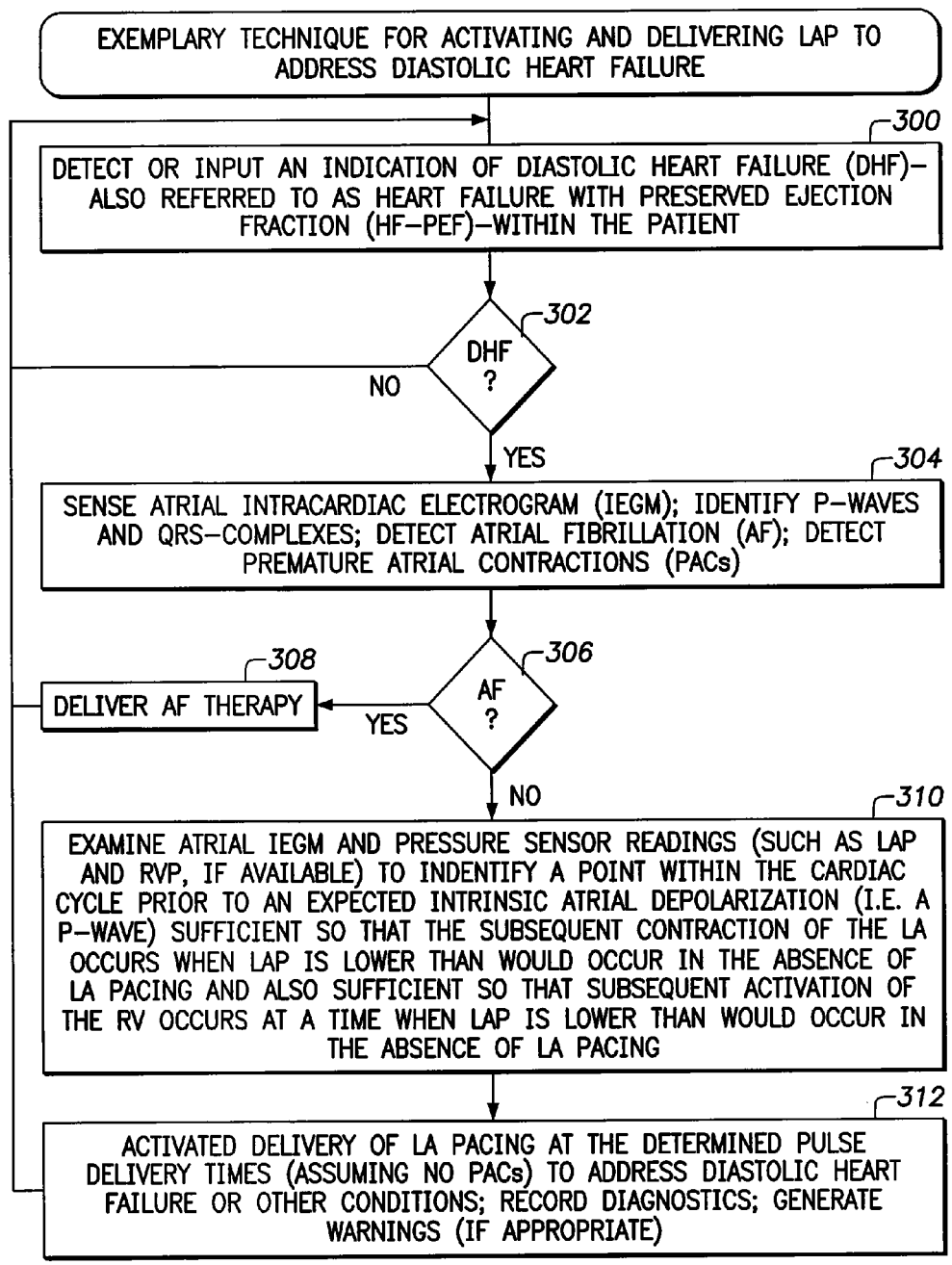
FIG. 5 provides a more detailed illustration of the LA pacing technique of FIG. 2.

Turning now to FIG. 5, an exemplary LA pacing technique will be described in more detail. Beginning at step 300, the CRMD detects or inputs an indication of DHF (i.e. HF-PEF) within the patient. In some embodiments, this indication is simply input into the CRMD by the clinician using an external programming device (assuming the clinician has rendered a diagnosis of DHF in the patient). However, in other embodiments, the CRMD may be equipped to detect an indication of DHF within the patient. For example, see the techniques described in: U.S. Patent Application 2006/0149155 of Hedberg, entitled "Detection of Diastolic Heart Failure"; U.S. Pat. No. 7,416,529 to Hedberg, also entitled "Detection of Diastolic Heart Failure"; U.S. Pat. No. 7,526,338 to Gill et al., entitled "Implantable Cardiac Device for Monitoring Diastolic Heart Failure and Method of Operation and Use Thereof"; U.S. Pat. No. 7,850,616 also to Gill et al., entitled "Determination of Diastolic Heart Failure"; and U.S. Patent Application 2008/0262365 of Bjorling, entitled "Detection and/or Monitoring of Diastolic Heart Failure."

Assuming that DHF is indicated at step 302, then the device at step 304 senses an atrial IEGM, identifies P-waves and QRS-complexes (i.e. R-waves), detects AF (based, for example, on the atrial rate exceeding a predetermined threshold), detects premature atrial contractions (PACs), etc. (Note that, the CRMD may perform these functions even in the absence of any indication of DHF as these are standard device functions). If AF is detected at step 306, the CRMD at step 308 then delivers AF therapy rather than initiating any LA pacing. Techniques for responding to AF are discussed, for example, in: U.S. Pat. No. 7,113,822 to Kroll, entitled "System and Method for Providing Cardioversion Therapy and Overdrive Pacing using an Implantable Cardiac Stimulation Device"; U.S. Pat. No. 7,289,847 to Gill et al., entitled "Implantable Cardiac Device and Method of Treating Atrial Fibrillation"; and U.S. Pat. No. 7,076,300 Kroll et al., entitled "Implantable Cardiac Stimulation Device and Method That Discriminates Between and Treats Atrial Tachycardia And Atrial Fibrillation."

Assuming, though, that there is no ongoing AF, then the CRMD at step 310 examines the atrial IEGM and pressure sensor readings (such as LAP and RV pressure (RVP) sensor readings, if available) to identify a point within the cardiac cycle prior to an expected intrinsic atrial depolarization (i.e. a P-wave) sufficient so that subsequent contraction of the LA occurs when LAP is lower than would occur in the absence of LA pacing and also sufficient so that subsequent activation of the RV occurs when LAP is lower than would occur in the absence of LA pacing. In one example, the CRMD determines when a next P-wave is expected (based, e.g., on current V-A intervals) and selects a preferred time prior to the expected P-wave for delivery of an LA pacing pulse. This may be performed in conjunction with AF suppression or "dynamic atrial overdrive" (DAO) pacing techniques. See, for example, DAO techniques described in: U.S. Pat. No. 6,519,493 of Florio et al., entitled "Methods and Apparatus for Overdrive Pacing Heart Tissue using an Implantable Cardiac Stimulation Device", issued Feb. 11, 2003. With DAO, the overdrive pacing rate is controlled to remain generally uniform and, in the absence of a tachycardia, is adjusted upwardly or downwardly only occasionally. The preferred timing of the LA pulse relative to an expected P-wave may be programmed, for example, by the clinician. In other examples, the device determines a preferred time for delivery of the LA pulse based on an examination or analysis of LAP and RVP pressure readings or other suitable signals or measurements. In this regard, the device can select or determine a preferred time for delivery of the LA pulse so that the LAP will be at its lowest at the time the RV ejects blood into the pulmonary artery (based, for example, on an examination of RVP signals within the patient).

RVP can be readily detected with a pressure transducer positioned in the RV along the RV lead. See, for example, U.S. Pat. No. 6,915,162 to Noren et al., entitled "Implantable Medical Device for Measuring Ventricular Pressure." LAP sensors (or proxies for estimating LAP) are discussed, e.g., in: U.S. Patent Application 2011/0208077 of Soriano et al., entitled "System and Method for Exploiting Atrial Electrocardiac Parameters in Assessing Left Atrial Pressure using an Implantable Medical Device"; U.S. Pat. No. 8,135,468 to Gutfinger et al., entitled "Systems and Methods for Estimating Left Atrial Pressure (LAP) in Patients with Acute Mitral Valve Regurgitation for use by an Implantable Medical Device"; U.S. Pat. No. 7,794,404 to Gutfinger et al., entitled "System and Method for Estimating Cardiac Pressure using Parameters Derived from Impedance Signals Detected by an Implantable Medical Device"; U.S. Patent Application 2009/0018597 of Wenzel et al., filed Jul. 18, 2007, entitled "System and Method for Estimating Cardiac Pressure based on Cardiac Electrical Conduction Delays using an Implantable Medical Device." See, also, U.S. Pat. No. 7,509,169 to Eigler et al., entitled "Implantable Pressure Transducer System Optimized for Anchoring and Positioning."

See, also, U.S. patent application Ser. No. 11/856,443, filed Sep. 17, 2007 of Zhao et al., entitled "MEMS-Based Left Atrial Pressure Sensor for use with an Implantable Medical Device" and U.S. patent Ser. No. 11/927,026 filed Oct. 29, 2007, entitled "Systems and Methods for Exploiting Venous Blood Oxygen Saturation in combination with Hematocrit or Other Sensor Parameters for use with an Implantable Medical Device", which also discussed transseptal physiological sensors.

At step 312, the CRMD then activates delivery of LA pacing at the determined (i.e. preferred) pulse delivery times (assuming no PACs) to address DHF or other conditions. The device also records diagnostics and generates warnings (if appropriate), etc. Insofar as PACs are concerned, if the CRMD detects a PAC prior to the time during the cardiac cycle when an LA pacing pulse is to be delivered, then the LA pulse is inhibited since the atria is already contracting. Insofar as diagnostics is concerned, information may be stored in the CRMD for subsequent review by a clinician pertaining to detection of DHF, AF, PACs, etc., and specifying the particular pulse delivery times the CRMD employed for LA pacing. Warnings may be generated to alert the clinician or caregiver regarding DHF, AF or other abnormal conditions.

What have been described are various techniques for delivering LA pacing to mitigate DHF or related conditions. These techniques may be applied, where appropriate, in conjunction with other techniques to address DHF or other related cardiopulmonary conditions. See, for example, techniques described in: U.S. Patent Application 2010/0256701 of Muller, entitled "Determining Site-To-Site Pacing Delay For Multi-Site Anti-Tachycardia Pacing"; U.S. Patent Application 2010/0069990 Muller et al., entitled "System and Method for Determining Atrioventricular Pacing Delay Based On Atrial Repolarization"; U.S. Pat. No. 7,643,878 Muller et al., entitled "System and Method for Determining Atrioventricular Pacing Delay based on Atrial Depolarization"; and U.S. Pat. No. 7,363,077 to Min et al., entitled "Adaptive timing interval control method for treating congestive heart failure."

For the sake of completeness, a detailed description of an exemplary CRMD for delivering LA pacing will now be provided, which is a pacer/ICD. However, principles of invention may be implemented within other CRMD implementations or within other implantable devices such as CRT-P devices or CRT-D devices. Furthermore, although examples described herein involve processing of data by the implanted device itself, some operations may be performed using an external device, such as a bedside monitor, device programmer, computer server or other external system. For example, detection of DHF and selection of preferred LA pulse delivery times may be made using an external device based on data received from the CRMD, which then send commands for controlling LA pacing back to the CRMD. Processing by the implanted device itself is generally preferred as that allows the device to respond more promptly and autonomously to DHF or other conditions.

Exemplary Pacer/ICD

Figure 6:
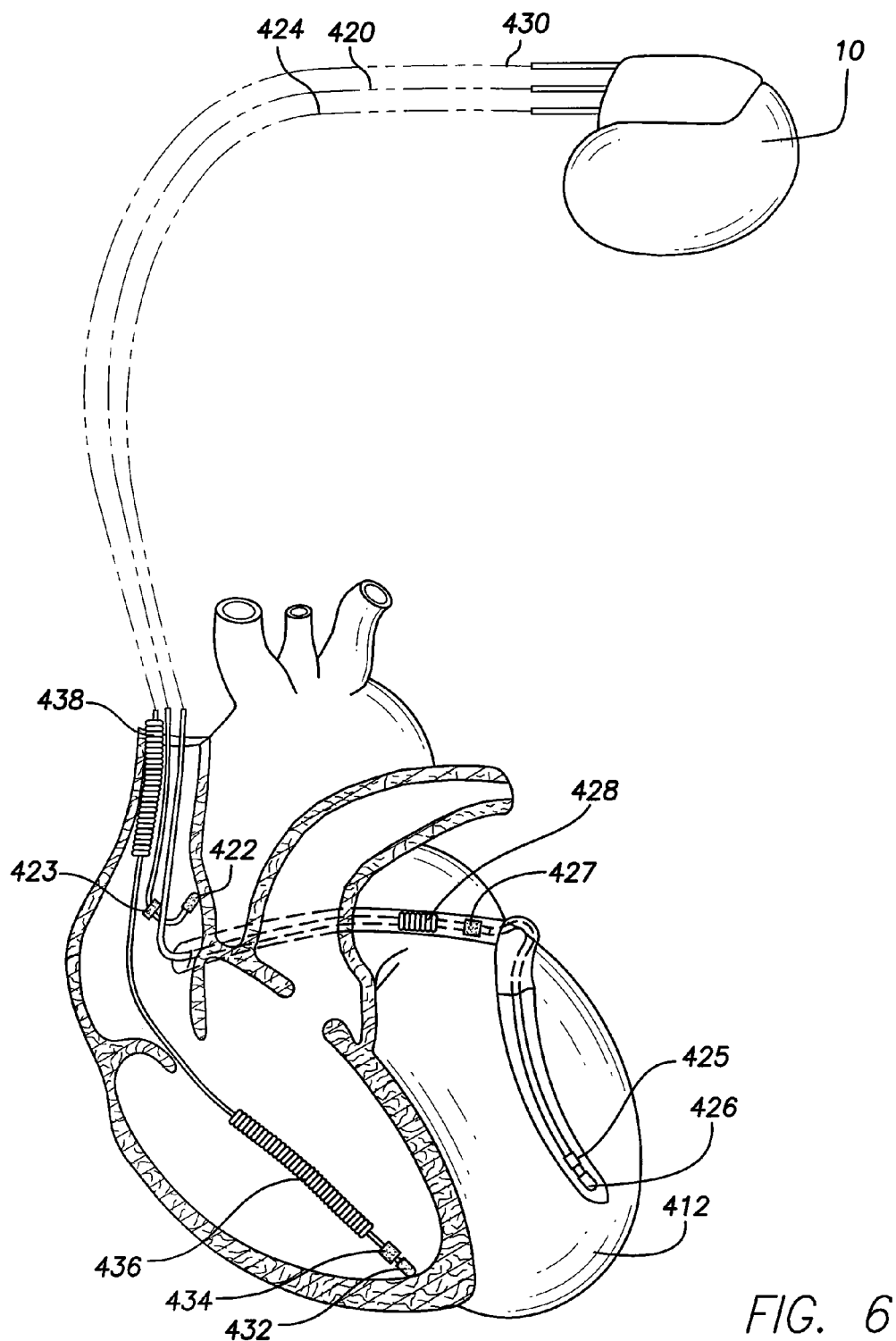
FIG. 6 is a simplified, partly cutaway view, illustrating the CRMD of FIG. 1 along with at set of leads implanted into the heart of the patient.

FIG. 6 provides a simplified block diagram of the pacer/ICD, which is a dual-chamber stimulation device capable of treating both fast and slow arrhythmias with stimulation therapy, including cardioversion, defibrillation, and pacing stimulation, as well as capable of controlling LA pacing as described above. To provide atrial chamber pacing stimulation and sensing, pacer/ICD 10 is shown in electrical communication with a heart 412 by way of a right atrial lead 420 having a right atrial tip electrode 422 and a right atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle. In some embodiments, an RVP pressure sensor is mounted to the RV lead.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. In particular, the aforementioned LA pacing may be delivered using LA electrode 427 (in combination with a suitable return electrode). With this lead configuration, LA pacing as well as biventricular pacing can selectively be performed. In some examples, an LAP pressure sensor (or sensor providing a proxy for LAP) is mounted to the LV/CS lead or is implanted transseptally into the LA via the RA lead.

Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 7:
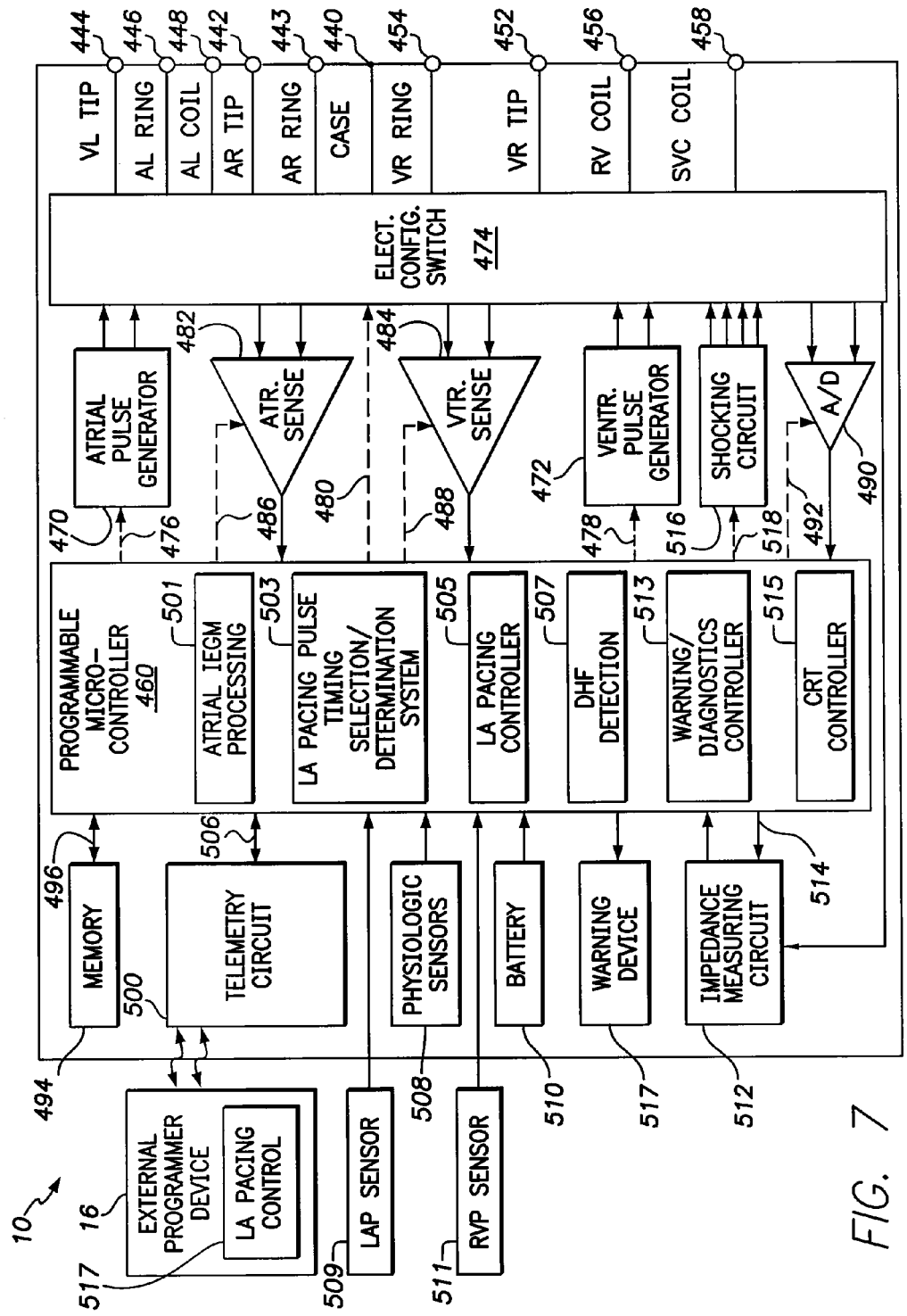
FIG. 7 is a functional block diagram of the CRMD of FIG. 6, illustrating basic circuit elements that provide cardioversion, defibrillation and/or pacing stimulation in the heart and particularly illustrating components for controlling LA pacing using the techniques of FIGS. 2-5.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned LA pacing functions.

The housing 440 for pacer/ICD 10, shown schematically in FIG. 7, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller itself are not critical. Rather, any suitable microcontroller 460 may be used to carry out the functions described herein. The use of microprocessor-based control circuits for performing timing and data analysis functions are well known in the art.

As shown in FIG. 7, an atrial pulse generator 470 and a ventricular/impedance pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses, including LA pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 16. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, the aforementioned thresholds as well as pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 16, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 16 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc. Also, as shown, one or more pressure sensors (509, 511) may be employed (external to the device can) for sensing RVP, LAP or other signals from which RVP or LAP can be estimated. Additional connection terminals may be needed to accommodate any external sensors.

The pacer/ICD additionally includes a battery 510, which provides operating power to all of the circuits shown in FIG. 7. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, pacer/ICD 10 is preferably capable of high voltage therapy and appropriate batteries.

As further shown in FIG. 7, pacer/ICD 10 is shown as having an impedance measuring circuit 512 which is enabled by the microcontroller 460 via a control signal 514. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 512 is advantageously coupled to the switch 474 so that any desired electrode may be used.

In the case where pacer/ICD 10 is intended to operate as an ICD device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules or more), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to controlling LA pacing. In particular, the microcontroller includes an atrial IEGM processing system 501 operative to sense atrial electrical cardiac signals; a LA pacing pulse timing selection/determination system 503 operative to determine pulse delivery times for delivery of LA pacing pulses sufficient, e.g., so that subsequent activation of the RV of the heart of the patient occurs when LA pressure is lower than would occur in the absence of LA pacing; and an LA pacing controller operative to control delivery of LA pacing using a stimulation electrode positioned near the LA at the determined pulse delivery times. If the CRMD is equipped to detect an indication of DHF, such detection may be performed or controlled by a DHF detection system 507. A warning/diagnostics controller 513 controls the generation of diagnostic data and warning signals pertinent to LA pacing or DHF. The diagnostic data is stored within memory 494. Warning signals may be relayed to the patient via internal warning device 517 or via external device 16. If equipped to perform CRT, a CRT controller 515 may be provided.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller. Note also that, in some implementations, the aforementioned ventricular relaxation rate detector and the ventricular compliance detector are not components of a diastolic function monitoring system but operate independently.

When used in conjunction with an external system, the external system can be equipped to perform some of the LA pacing control functions described herein (such as detection of DHF or selection of the preferred times for LA pacing) by analyzing data transmitted from the pacer/ICD. This is generally indicated by way of LA pacing controller 517 of the external device.

What have been described are various systems and methods for use with a CRMD or an external system used in conjunction with a CRMD. However, principles of the invention may be exploiting using other implantable medical systems. Thus, while the invention has been described with reference to particular exemplary embodiments, modifications can be made thereto without departing from the scope of the invention.

What is claimed is:

1. A method for use with an implantable medical device having a stimulation electrode positioned for delivering left atrial pacing stimulation, the method comprising:
   sensing electrical cardiac signals;
   determining pulse delivery times for delivery of left atrial pacing pulses sufficient so that subsequent activation of the right ventricle of the heart of the patient occurs when left atrial pressure is lower than would occur in the absence of left atrial pacing; and
   delivering left atrial pacing using the stimulation electrode at the determined pulse delivery times.

2. The method of claim 1 wherein the pulse delivery times are also sufficient so that activation of the left atrium occurs when left atrial pressure (LAP) is lower than would occur in the absence of left atrial (LA) pacing.

3. The method of claim 1 wherein determining the pulse delivery times for delivery of LA pacing pulses times includes:
   identifying at least one cardiac cycle within the electrical cardiac signals; and
   identifying a time during the cardiac cycle prior to an intrinsic depolarization of the atria for delivery of a LA pacing pulse.

4. The method of claim 3 for use with a diastolic heart failure (DHF) patient wherein identifying the time for delivery of the LA pacing pulse is performed to identify a pulse delivery time sufficient to mitigate the DHF.

5. The method of claim 3 further including a preliminary step of detecting an indication of DHF within the patient and activating the delivery of LA pacing in response to the indication of DHF.

6. The method of claim 1 further including detecting atrial fibrillation (AF) and wherein delivery of LA pacing is inhibited in the presence of atrial fibrillation.

7. The method of claim 1 wherein all of the steps are performed by the implantable medical device.

8. The method of claim 1 wherein at least some steps are performed by an external system in communication with the implantable medical device.

\* \* \* \* \*